(12) United States Patent
Proksa et al.

(10) Patent No.: US 12,329,464 B2
(45) Date of Patent: Jun. 17, 2025

(54) SPECTRAL DUAL-LAYER CT-GUIDED INTERVENTIONS

(71) Applicant: KONINKLIJKE PHILIPS N.V., Eindhoven (NL)

(72) Inventors: Roland Proksa, Hamburg (DE); Alexander André Fingerle, Munich (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1043 days.

(21) Appl. No.: 17/270,461

(22) PCT Filed: Aug. 28, 2019

(86) PCT No.: PCT/EP2019/072993
§ 371 (c)(1),
(2) Date: Feb. 23, 2021

(87) PCT Pub. No.: WO2020/043789
PCT Pub. Date: Mar. 5, 2020

(65) Prior Publication Data
US 2021/0251699 A1    Aug. 19, 2021

(30) Foreign Application Priority Data
Aug. 28, 2018   (EP) .................................... 18191114

(51) Int. Cl.
*A61B 34/20*   (2016.01)
*A61B 6/00*    (2006.01)
(Continued)

(52) U.S. Cl.
CPC .............. *A61B 34/20* (2016.02); *A61B 6/032* (2013.01); *A61B 6/461* (2013.01); *A61B 6/50* (2013.01); *A61B 6/54* (2013.01)

(58) Field of Classification Search
CPC ......... A61B 34/20; A61B 6/032; A61B 6/461; A61B 6/481; A61B 6/482; A61B 6/50; A61B 6/507; A61B 6/54
See application file for complete search history.

(56) References Cited

U.S. PATENT DOCUMENTS 6,650,928 B1 * 11/2003 Gailly .................... A61B 6/504
                                                    600/431
2003/0174806 A1 * 9/2003 Francke ................. A61B 6/502
                                                    378/37
(Continued)

FOREIGN PATENT DOCUMENTS

DE   102007024450 A1   11/2008
WO   WO2013011418 A2   1/2013
WO   WO2014128595 A1   8/2014

OTHER PUBLICATIONS

Ao Li et al., "Superparamagnetic perfluorooctylbromide nanoparticles as multimodal contrast agent for US, MR, and CT imaging," Apr. 1, 2013, Acta Radiologica,, pp. 278-283 (Year: 2013).*
(Continued)

*Primary Examiner* — Ashley K Buran
*Assistant Examiner* — Maria Christina Talty
(74) *Attorney, Agent, or Firm* — Larry Liberchuk

(57) ABSTRACT

A method of spectrally imaging an organ during an image-guided intervention is disclosed. Based on at least one first scan, a first image modality is obtained. A selection of a region of interest is obtained within the first image modality. Based on at least one second spectral scan of the organ, at least three second image modalities are obtained. A contrast value is calculated over the previously selected region of interest for all obtained second image modalities. The second image modality with the largest contrast value is selected for display. Alternatively, image modalities of the organ are displayed over time and the modalities for display (Continued)

are selected according to an imaging protocol which associates a lesion type and timestamp of a spectral scan with a modality having optimal contrast.

14 Claims, 2 Drawing Sheets

(51) Int. Cl.
*A61B 6/03* (2006.01)
*A61B 6/46* (2024.01)
*A61B 6/50* (2024.01)

(56) References Cited

U.S. PATENT DOCUMENTS

| | | | |
|---|---|---|---|
| 2011/0282194 A1* | 11/2011 | Reiner | G16H 50/70 600/431 |
| 2012/0140893 A1* | 6/2012 | Feuerlein | A61B 6/542 378/108 |
| 2013/0308847 A1* | 11/2013 | Schirra | G06T 7/0012 382/131 |
| 2015/0221082 A1* | 8/2015 | Carmi | A61B 8/5223 382/128 |
| 2016/0183896 A1 | 6/2016 | Muller | |
| 2017/0148156 A1 | 5/2017 | Bregman-Amitai | |
| 2018/0042681 A1 | 2/2018 | Jagga | |
| 2018/0165812 A1* | 6/2018 | Flohr | G06T 11/005 |

OTHER PUBLICATIONS

PCT International Search Report, International application No. PCT/EP2019/072993, Nov. 21, 2019.

Muenzel D. et al., "Photon Counting CT of the Liver with Dual-Contrast Enhancement", Proceedings of SPIE, vol. 978 3, Mar. 22, 2016 (Mar. 30, 2016), p. 97835N, XP055558801.

Bongers M.N. et al., "Noise-Optimized Virtual Monoenergetic Images and Iodine Maps for the Detection of Venous Thrombosis in Second-Generation Dual-Energy CT (DECT): An Ex Vivo Phantom Study", Computed Tomography, Eur Radiol 25:1655-1664, Aug. 21, 2014.

Rajiah P. et al., "Benefit and Clinical Significance of Retrospectively Obtained Spectral Data with a Novel Detector-Based Spectral Computed Tomography—Initial Experiences and Results", Clinical Imaging, pp. 65-72, Jun. 26, 2017.

* cited by examiner

SPECTRAL DUAL-LAYER CT-GUIDED INTERVENTIONS

FIELD OF THE INVENTION

The present invention relates to a spectral imaging method generally and to spectral imaging by dual-layer CT for guidance more particularly.

BACKGROUND OF THE INVENTION

Conventional CT imaging techniques are sometimes facing the problem of no or little visual contrast of a liver lesion over the surrounding tissue, a problem which is peculiar to organs like the liver or the kidney. Contrast-enhanced CT mitigates this problem partially, but, in turn, faces the problems of declining concentrations of injected contrast agents due to renal excretion, complex contrast agent dynamics during different uptake conditions, as well as washout of the contrast agent in a delayed phase after injection. In consequence, a visual contrast may be vanishing quickly or may become inappropriate under a changing uptake condition at a moment of time, which may cause the failure of interventions which target the contrast-enhanced lesion and use CT for guidance, in particular liver or kidney interventions. Therefore, there is still need for good imaging methods of organs like the liver which yield improved contrast and maintain it over longer periods of time.

SUMMARY OF THE INVENTION

It is an object of embodiments of the present invention to provide good spectral imaging methods of a contrast-enhanced liver and devices configured to carry them out. A spectral imaging method of the present invention is useful for guidance of a physician performing an intervention for lesions in organs with complex contrast agent dynamics, such as the liver or the kidneys, because it dynamically adapts a displayed image modality, thereby improving visual contrast of a liver lesion over extended periods of time, which makes planned liver interventions safer and their success rates more likely.

The above objective is accomplished by a method and device according to the present invention.

In a first aspect, the present invention relates to a method for spectrally imaging an organ during an image-guided intervention. The method comprises displaying a first image modality of a contrast-enhanced organ based on at least one first scan of the contrast-enhanced organ. The first image modality may be obtained by first performing a first spectral or other image modality scan of the contrast-enhanced organ and by subsequently performing a reconstruction for deriving the first image modality from the spectral projection data. Alternatively, it may be obtained as data from a data source, such as, for example, a memory. The first image modality may thus for example originate from an archived scan. The method also comprises selecting a region of interest within the displayed first image modality. Optionally, the first scan can be of a different modality, in which the region of interest can be indicated. The method then further determines contrast values for at least three second image modalities of the contrast-enhanced organ based on an at least one second spectral scan of the contrast-enhanced organ and determining a contrast value over the region of interest for each of the at least three second image modalities. Optionally, the three second image modalities are obtained and the contrast values are determined using image processing means. The method also comprises selecting the one of the at least three second image modalities with the largest contrast value and (if not already done so: obtaining and) displaying it, thereby providing a dynamic adaptation of the displayed image modality such that a time interval available for reliably guiding the intervention, before washout of the contrast agent, is prolonged.

This spectral imaging method has the advantage that an intervening physician or radiologist is, at every moment of the intervention, provided visual feedback with improved visual contrast, which increases reliability and success of such intervention. Changing conditions in the uptake of the contrast agent due to the complex dynamics of contrast agents in some organs are actively compensated for. Processing means are typically programmed to analyze and to select largest contrast in a fast and automated way, thereby achieving real-time updates of displayed image modalities with contrast adjustment over time, which eases the intervention. Optionally, a displayed image contrast may be boosted or enhanced for better visual perception if the determined contrast value over a region of interest is falling below a predetermined threshold value.

Image-guided interventions may comprise spectral CT-guided, e.g. dual-layer CT, liver biopsies for which the lesion from which a test sample is taken is well distinguishable from the surrounding liver parenchyma.

Selecting a region of interest may advantageously reduce the processing resources spent on analyzing contrast in image modalities and/or reconstructing image modalities. A selected image modality may, in consequence, displayed faster or in shorter intervals.

Spectral scans, the display of a first and further image modalities or the start of the image-guided method may be triggered by a suitable triggering means, which may include voice command or foot pedals. Therefore, the intervening physician or radiologist can decide on the best moment to start the intervention and also enjoys the benefit of having his or her hands free to manipulate additional devices, such as aspiration needles and the like, which also presents a gain of time in a time-limited intervention. The at least one second spectral scan may be triggered automatically after performing the at least one first scan with a predetermined time delay.

Image modalities selected for display may include spectral image modalities like virtual non-contrast, effective atomic number, iodine, monoenergetic at a predetermined energy level. This provides a plurality of image modalities which cover a wide range of uptake conditions of contrast agents in different organs and for different lesion types and elemental compositions. Monoenergetic energy levels may range between 40 keV and 120 keV. These advanced imaging modalities may be applied to 2D or 3D image data for better visualization of the organ or lesion. A peculiar feature of these advanced techniques is presented by the fact that irrelevant or distracting elements may be removed or subtracted from the displayed image, for instance capillary blood vessels supplying the lesion or organ.

In a second aspect, the present invention relates to an alternative method for spectrally imaging an organ during an image-guided intervention. The alternative method comprises displaying different second image modalities of a contrast-enhanced organ over time, where a lesion type from a predetermined set of lesion types is pre-detected for the imaged organ. The second image modalities are based on a timestamped spectral scan of the contrast-enhanced organ. In the alternative method the selection of one of the at least three second image modality is performed according to a pre-determined lesion-dependent imaging protocol. The imaging protocol for a certain lesion type describes the expected behavior of the contrast ratios of the second image modalities over time. The alternative method comprises obtaining a plurality of sets on which the at least three second image modalities can be based. Each spectral sample scan is also timestamped with respect to a reference time. Expected contrast values in a region of interest around the lesion are determined based on the time stamp and on the imaging protocol and are used to select which of the at least three second image modalities should be selected and displayed as the modality with the (likely) largest contrast value in the region of interest.

This method facilitates the sharing and portability of standard imaging protocols for a large variety of lesions encountered in image-guided interventions. It also benefits from the expertise input of experienced radiologists selecting the region of interests for each lesion type and assessing appropriate contrast values. Furthermore, the imaging protocols are easily referenced during an intervention and this method requires only reconstruction of one second image modality from the second spectral scan, as compared to the more time-consuming process of obtaining at least three different image modalities according to the method of the first aspect.

In the method, a predetermined set of lesion types may comprise at least the set of metastasis, hepatocellular carcinoma of type I, hepatocellular carcinoma of type II, Hemangioma, cyst.

In the method, a reference time for timestamping spectral scans may be determined as the moment in time at which the contrast agent is injected.

The present invention further relates to a controller adapted for performing steps of a method as described above except for the display steps. The present invention also relates to a spectral scanning system comprising such a controller.

Particular and preferred aspects of the invention are set out in the accompanying independent and dependent claims. Features from the dependent claims may be combined with features of the independent claims and with features of other dependent claims as appropriate and not merely as explicitly set out in the claims.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, in which.

Figure 1:
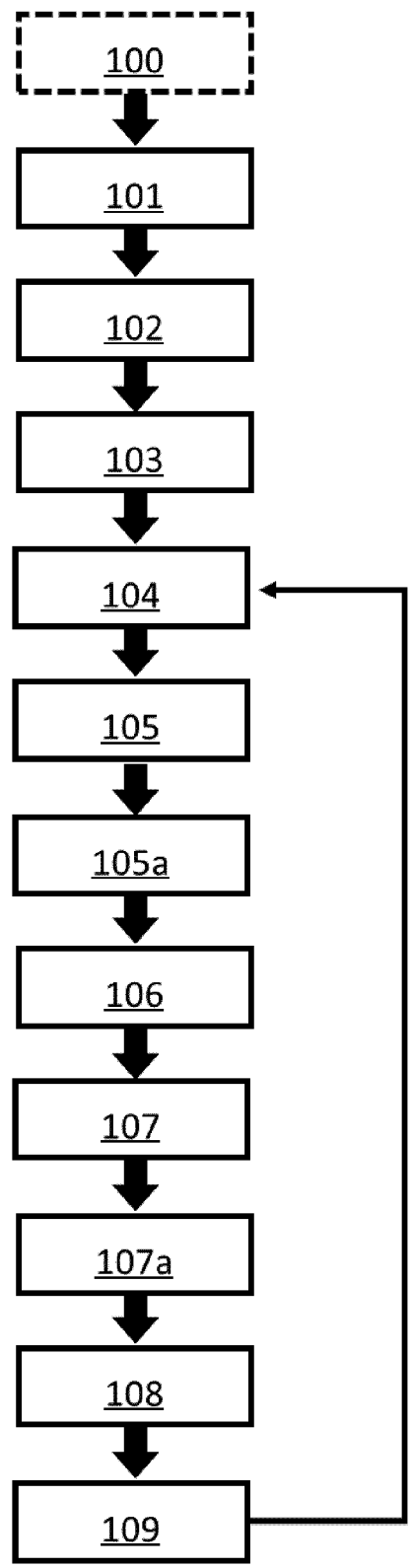
FIG. 1 shows a flow diagram of steps of a spectral imaging method according to an embodiment of the present invention.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention.

Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art.

It should be noted that the use of particular terminology when describing certain features or aspects of the invention should not be taken to imply that the terminology is being re-defined herein to be restricted to include any specific characteristics of the features or aspects of the invention with which that terminology is associated.

In the description provided herein, numerous specific details are set forth. However, it is understood that embodiments of the invention may be practiced without these specific details. In other instances, well-known methods, structures and techniques have not been shown in detail in order not to obscure an understanding of this description.

Definitions

A patient may be a human or an animal. An imaging method according to the present invention is suitable for guiding a physician during an intervention, e.g. a liver biopsy or aspiration. Although an imaging method according to the present invention can be performed concurrently with a surgical intervention it is typically part of, the present imaging method remains a self-contained imaging method. Whereas administering a CT contrast agent may typically be performed for performing the imaging method, the step of administering the CT contrast agent typically may be outside the imaging method and therefore may not form a step of the imaging method.

In a first aspect, the present invention relates to a method for spectrally imaging an organ during an image-guided intervention. The method comprises displaying a first image modality of a contrast-enhanced organ based on at least one first scan of the contrast-enhanced organ. The first image modality may be obtained by first performing a first spectral scan of the contrast-enhanced organ and by subsequently performing a reconstruction for deriving the first image modality. Alternatively, it may be obtained as data from a data source, such as, for example, a memory. The first image modality may thus for example originate from an archived scan. The method also comprises receiving a selection of a region of interest within the displayed first image modality. Optionally, the first scan may be of a different modality, in which the region of interest can be indicated. The method then further comprises obtaining at least three second image modalities of the contrast-enhanced organ based on an at least one second spectral scan of the contrast-enhanced organ and determining a contrast value over the region of interest for each of the at least three second image modalities, using image processing means. The method also comprises selecting the one of the at least three second image modalities with the largest contrast value and displaying it, thereby providing a dynamic adaptation of the displayed image modality such that a time interval available for reliably guiding the intervention, before washout of the contrast agent, is prolonged.

By way of illustration, embodiments of the present invention not being limited thereto, standard and optional elements of methods according to embodiments are further discussed below with reference to an exemplary method.

Reference is made to FIG. 1. A contrast agent may have been administered 100 to the patient orally or intravenously in a soluble form, e.g. as a prepared solution containing a predetermined concentration of a CT contrast agent, such as iodine or gadolinium. This moment in time at which the contrast agent is administered 100, e.g. injected, defines a reference time during an imaging method in accordance with embodiments of the present invention. Administrating CT contrast agents 100, even intravenously at a peripheral location (e.g. arm), is considered a safe clinical routine procedure, which is often carried out by trained health care professionals. In consequence, there are only little and limited health risks and accompanying side effects involved. In particular, allergies based on the agent substance itself can be ruled out by a preparatory evaluation of the patient's personal health status. Only the resulting condition of the step of administering a contrast agent 100, i.e. a contrast-enhanced liver, meaning that a contrast agent has been taken up in a liver, is a feature of the present imaging method according to embodiments of the present invention.

Although the following detailed description is referring to the liver and liver interventions, such as liver biopsies, other organs which show complex contrast agent dynamics and/or different uptake conditions and phases may be spectrally imaged according to the embodiments of the present invention. Kidneys are another non-limiting example for organs, in particular non-mammal kidneys with a renal portal venous system.

The blood circulatory system of the liver is special in many ways, which affects the uptake of intravenous contrast. It is important to note, for example, the fact that the liver has a portal venous system. The hepatic portal system receives the partially deoxygenated blood of the gastrointestinal tract, in large parts via the portal vein, which is subsequently drained to the hepatic vein. As one of the rare organs with dual blood supply, the liver also receives oxygen-rich blood through the hepatic artery. Yet, normal liver parenchyma is supplied to about 80% by blood of the portal vein and only to about 20% by artery blood. In consequence, the liver parenchyma enhances maximally in the hepatic phase or portal venous phase about 70 seconds to 80 seconds past injection and only little in the late arterial phase about 35 seconds to 40 seconds past injection. This is in contrast to hypervascular lesions on the one hand, such as Hepatocellular carcinoma (HCC), focal nodular hyperplasia, adenoma and hemangioma, which are primarily supplied by oxygen-rich blood of the hepatic vein and therefore optimally enhance in the later arterial phase during which the liver background, i.e. the parenchyma, only shows little enhancement. On the other hand, hypovascular lesions being only poorly supplied with blood, such as cysts, abscesses and metastases, are best differentiated during the hepatic phase during which the surrounding liver parenchyma is increasingly enhanced. Fibrotic lesions may be best differentiated in a delayed phase (e.g. 6 to 10 minutes past injection) during a contrast-enhanced CT scan because they are characterized by a poor washout of the contrast agent. In any case, contrast enhancement is significantly reduced or washed out during the excretory and delayed phase due to a declining concentration of the contrast agent being excreted and/or an equalization of the contrast agent throughout the different tissues.

Based on the foregoing observations, it becomes clear that intravenous contrast is typically used to increase the otherwise low inherent contrast between focal lesions, e.g. tumors, and the surrounding parenchyma and that the vanishing of a visual contrast enhancement may cause difficulties and failures when carrying out liver biopsies, aspirations, or other liver interventions that require an optimal visual contrast to identify the lesion and to guide a surgeon in the correct placement of a needle. Therefore, a spectral CT imaging method which is capable of dynamically adapting the displayed image of the liver lesion so as to provide improved visual contrast in real-time for guiding a surgeon has the potential of increasing the success rate of liver intervention. An additional advantage of such spectral CT imaging method is that the time window available to carry out such a liver intervention before the contrast agent washes or declines to a level where the targeted lesion is not visible any longer, may be increased by artificially boosting the image contrast or by providing an image modality that has improved visual contrast.

A contrast-enhanced liver is spectrally scanned at a first time 101. Therefore, a patient or animal may rest on a support structure which is moved through a spectral CT scanner, e.g. in a helical scanner. The first spectral scan 101 may be initiated by a health care professional or the radiologist, e.g. manually, via voice command or by means of a foot pedal. Intravenous injection of the contrast agent 100 may be initiated in an analogous manner. Referencing time in respect of the moment at which intravenous injection of the contrast agent starts, a first time for performing a spectral CT scan may correspond to a late arterial phase for hypervascular lesions, e.g. 35 second to 40 seconds past injection, or to a hepatic phase for a hypovascular lesion, e.g. 70 seconds to 80 seconds past injection. However, a different first time may be selected for performing the first spectral CT scan, depending on factors like the CT scanner, the concentration and injection speed of the contrast agent, the CT scan protocol, the lesion type, etc. It is also possible to perform two first spectral scans, e.g. one in the late arterial phase and one in the hepatic phase, or one prior to injection of the contrast agent and one in the hepatic phase. This may be advantageous for first coarsely locating the liver or abdomen and then perform a finer liver scan, or for coarsely placing and orienting a needle before approaching safely the lesion which is optimally enhanced at a later time.

From the first spectral scan, which may include a plurality of exposures at different angles and/or translational positions of the spectral CT scanner, energy-resolved projection data is obtained. A first image modality is reconstructed 102 based on the obtained energy-resolved projection data. Reconstruction algorithms may include (multi-) material decomposition combined with image reconstruction algorithms, e.g. based on the back-projection filtration framework (FBP), algebraic reconstruction technique (ART), model-based iterative reconstruction, or statistical algorithms, e.g. penalized likelihood.

The first image modality may be a conventional CT image, e.g. displaying Hounsfield units (HU) or CT numbers as grayscales. However, exploiting the energy-resolved detection of spectral CT, the first image modality may also be provided as one of the group of mono-energetic image at a predetermined X-ray energy level, effective atomic number (Z-effective) image, virtual non-contrast (VNC) image, material specific image, e.g. fat or iodine. If mono-energetic image modalities are obtained, energy levels may be ranging from 40 keV to 120 keV.

A physician or radiologist in charge of the liver intervention, or a trained employee under the supervision of the physician or radiologist, selects a region of interest 103 based on the reconstructed set of image modalities. The region of interest may be box-shaped, circular, or of any other shape, and encompasses the lesion under examination. If volumetric image information is reconstructed, the region of interest is selected correspondingly as a 3D box, sphere, etc. It is advantageous to only select a region of interest around the lesion as this reduces the number of exposures and a radiation dose received by the patient. It also accelerates the reconstruction of subsequent image modalities restricted to that smaller area or volume. Defining an appropriate region of interest 103 affects the later selection of displayed image modalities because improved visual contrast is determined with respect to the region of interest. This guarantees that the lesion is optimally differentiated from the surrounding liver tissue.

Next, at least one second spectral CT scan of the contrast-enhanced liver is performed at a second time 104. Typically, a plurality of second spectral CT scans are performed sequentially at regular intervals or in a pseudo-continuous manner, whereby a constantly updated image modality of the liver, and the lesion in particular, facilitates and guides the physician or radiologist during the intervention, e.g. by having continuous visual feedback of the lesion and a placed needle at improved contrast. The second spectral CT scan may be initiated automatically with a given adjustable delay with respect to the first scan, or may be initiated by the physician or radiologist when he or she is ready to carry out or proceed with the intervention. The second time, with respect to the reference time, may fall into the late arterial phase, the hepatic phase, or even later phases. The at least one second spectral CT scan gathers energy-resolved second projection data from which at least three different image modalities are reconstructed 105. Reconstruction algorithms available for reconstructing the at least three different image modalities may include the algorithms listed in relation to the reconstruction of the first image modality of the first spectral scan. Similarly, the at least three different image modalities may be selected from the non-exhaustive, but predetermined group of mono-energetic image at a predetermined X-ray energy level, effective atomic number (Z-effective) image, virtual non-contrast (VNC) image, material specific image, e.g. fat or iodine.

For each one of the at least three different image modalities (e.g. Z-effective, VNC, and mono-energetic), a contrast value is determined 106 inside the previously defined region of interest. A contrast value may be obtained as a contrast ratio of maximum signal to minimum signal within the region of interest, as contrast ratio of maximum signal inside the lesion to average signal outside the lesion, but within the region of interest, as contrast ratio of average signal inside the lesion to average signal outside the lesion, but within the region of interest, an average signal-to-noise ratio, or any other signal ratios derivable form the reconstructed image modality. Alternatively, the contrast value of each of the at least three image modalities may also take into account statistical information of the reconstructed image, e.g. the standard deviations of grayscale values or CT numbers with respect to an area inside and/or outside the lesion. For instance, the following contrast value may be calculated: contrast-to-noise ratio $$CNR = (HU\_lesion - HU\_parenchyma)/(0.5*(stddevHU\_lesion + stddevHU-parenchyma)).$$

Optionally, the contrast value may only be determined after an image filter or a sequence of filters 105a has been applied to the reconstructed at least three image modalities, for instance a noise-removal/denoising filter, smoothing filter, moving-average filter, median filter, edge enhancement filter, etc., or any combination thereof.

Reconstruction of image modalities and the calculation of contrast values is typically carried out by image processing means, but which may be different processing means. For instance, it may be of advantage to run the computationally intensive reconstruction algorithms on dedicated acceleration hardware, e.g. GPUs or GPU arrays, special purpose signal processors, etc. Calculation of the contrast values may also be achieved by a controller.

A controller is programmed to select the image modality with the largest contrast value 107 among the at least three reconstructed image modalities for display. The so selected image modality 107 is sent to a display device, e.g. screen or monitor, for dynamically updating a displayed image modality 108 of the liver, and in particular of the region of interest comprising the contrast-enhanced lesion. This ensures the timely (e.g. real-time or at short intervals) adaption of the displayed image modality such that an intervening physician or radiologist looking at it is always guaranteed to have improved visual contrast, even in the case of a declining concentration of a contrast agent and/or washout. Optionally, the image modality selected for display may undergo a contrast boosting step 107a if the determined largest contrast value is falling below a predetermined threshold level, e.g. if the contrast value is crossing the human contrast sensitivity function A (f) measuring the inverse contrast threshold value (contrast sensitivity) as a function of cycles per degree (e.g. obtained in Fourier space), e.g. A (f) as defined by Manos and Sakrison: A (f)=2.6*(0.0192+0.114*f)*[exp(−0.114*f)^1.1]. This threshold level may be adjusted to the needs and visual acuity or human contrast sensitivity function of the intervening physician or radiologist such that a vanishingly small visual contrast of the displayed image modality is artificially increased, thereby providing a longer lasting time window during which the liver intervention, e.g. biopsy, may be successfully performed. The contrast boosting step 107a may furthermore include the step of applying additional visual guiding aids, e.g. colored overlays delimiting the lesion and/or the needle, arrows indicating an orientation correction of the needle or a shortest path between the tip of the needle and the lesion.

In 109 the controller may, depending on a decision of the physician or radiologist, or on a current time, repeat another second spectral scan 104, reconstruction of image modalities 105, determination of contrast values 106, and selection of the image modality with the largest contrast value for display 107, it may delay or stall such a repetition (e.g. depending on the imaging protocol of the CT scanner), or it may end the spectral imaging method of the liver, e.g. at the end of the liver intervention or in case of abortion.

In some embodiments, a signal representative of the hypo- or hypervascular nature of a lesion may be derived, based on the determined contrast value of the displayed image modality, but not limited thereto. For example, shape information and/or uniformity may also be taken into account when deriving said signal.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Figure 2:
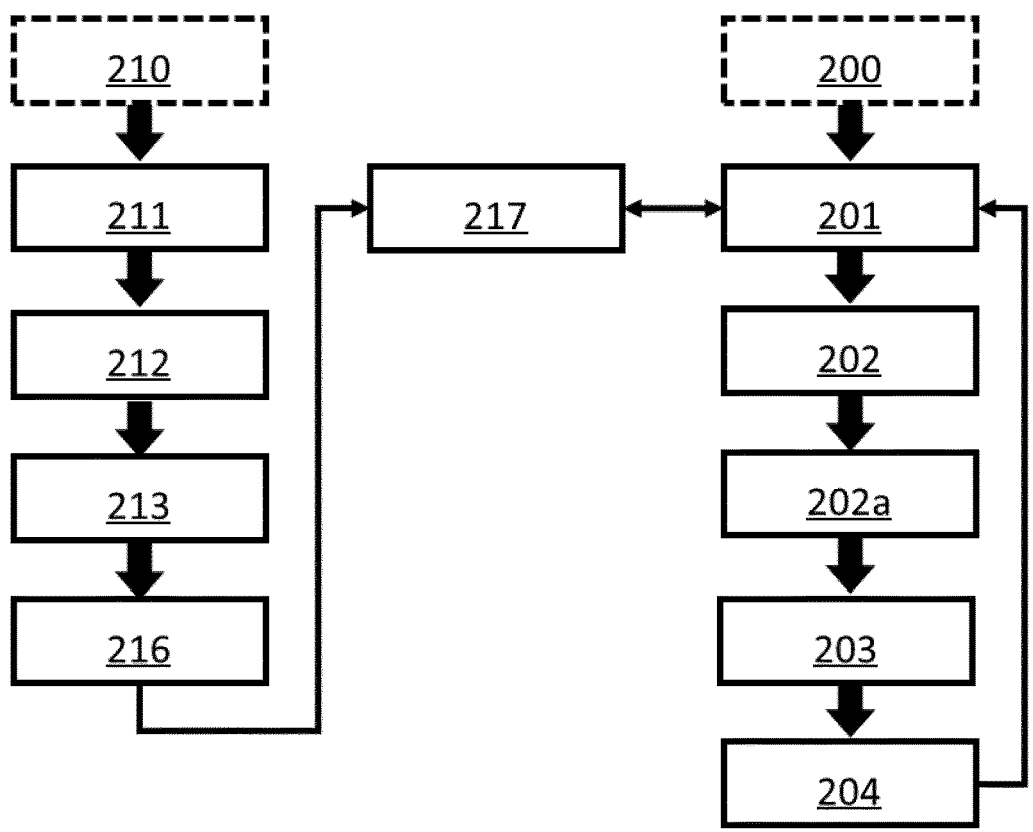
FIG. 2 shows a flow diagram of steps of a spectral imaging method according to an alternative embodiment of the present invention.

For example, it is possible to carry out a spectral imaging method of the present invention as described hereinafter in reference to FIG. 2.

Similarly to the step 100 of the first embodiment in FIG. 1, a patient has been administered orally or intravenously a contrast agent 200, e.g. iodine or gadolinium. The administering step 200 is not integral part of the present embodiment, only its resulting condition, a contrast-enhanced organ, e.g. liver, is a feature of the invention. A plurality of timestamped spectral CT scans is performed 201, repeatedly or at regular intervals, of a contrast-enhanced organ (e.g. liver) with a predetermined lesion type and time is measured in respect of a reference time, e.g. the start of injection of the contrast agent. Particular aspects of the spectral scans are analogous to the spectral scan 201 performed in FIG. 1, except for the fact that the lesion type is known beforehand for the scanned organ. Making use of one of the previously mentioned reconstruction algorithms an image modality for display is reconstructed 202 and displayed 203, e.g. displayed to an intervening physician or radiologist on a screen or monitor, in a subsequent step. Optionally, the contrast of the reconstructed image modality may be artificially boosted 202a if it falls below a visually perceptible threshold and/or may add further visual aids for guidance to the image modality for display. A controller may be programmed to take one of the following actions 204, with or without the input of an intervening physician or radiologist: initiate another timestamped spectral CT scan of the contrast-enhanced organ (e.g. liver) 201, followed by another reconstruction of an image modality for display 202 and updating/displaying the next image modality 203, stall or delay such a repetition, abort or interrupt the imaging method.

In the present embodiment, however, the specific image modality (e.g. Z-effective, VNC or mono-energetic) leading to improved visual contrast in the displayed, reconstructed image modality is determined in a different way. In particular, it is not necessary to reconstruct at least three different image modalities, as it was the case in the step 205 in FIG. 1, but one image modality suffices. In the present embodiment of FIG. 2, an imaging protocol has been established 217 before the spectral imaging of the contrast-enhanced organ starts. The imaging protocol communicates the specific modality for reconstruction to a reconstruction unit comprising processing means. A specific reconstruction modality is unambiguously determined by the imaging protocol if the timestamp of the current spectral CT scan and the lesion type are known inputs. That is obtained by associating, in the framework of a previously generated imaging protocol 217, a timestamp (in respect of a reference time) and a lesion type with a reconstruction modality for which the expected best visual contrast is obtained in the corresponding reconstructed image modality. Interpolation may be used to match a current timestamp with timestamps registered or stored inside the generated imaging protocol. An expected best visual contrast (e.g. largest CNR) may be derived statistically comparing many previously collected sample image modalities which have been obtained at that particular timestamp under similar scan conditions for the same type of lesion. An imaging protocol is thus generated for a predetermined set of lesion types, wherein the set may include, but is not limited to the following indications: HCC with various appearances, metastasis, hemangioma, cyst.

Generating an imaging protocol 217 may comprise the following steps. Patients for which one of the above listed lesions has been found or is expected to be found are administered a contrast agent 210. A plurality of timed spectral sample CT scans is performed 211 for each patient, and therefore for each lesion type, under reproducible conditions. A reference time for the timestamps may be the start of the injection of the contrast agent. A trained radiologist then defines a region of interest 213 around the contrast-enhanced lesion in each reconstructed sample image modality 212. It is pointed out that for scanned each patient/lesion type all the predetermined modalities of reconstruction (e.g. VNC, Z-effective, and mono-energetic) are exhausted at every timestamp of that particular scan. Thereafter, image processing means calculate a contrast value 216 over the defined region of interest for each reconstructed image modality, which includes each timestamp and each lesion type. At this point, a statistical ensemble of reconstructed image modalities is available, which is categorized by lesion type and timestamp. One may then assign a reconstruction modality to each lesion type and timestamp (dynamical variable) for which a best visual contrast is expected, based on the image modality that achieves the largest average contrast value for that particular lesion type and timestamp. Alternatively, one may assign a reconstruction modality to each lesion type and timestamp for which a best visual contrast is expected, based on the image modality that achieves the largest population count for that particular lesion type and timestamp, wherein a population count counts, among the ensemble of patients having that particular lesion type, the number of times an image modality is selected as having the largest contrast value.

Figure 3:
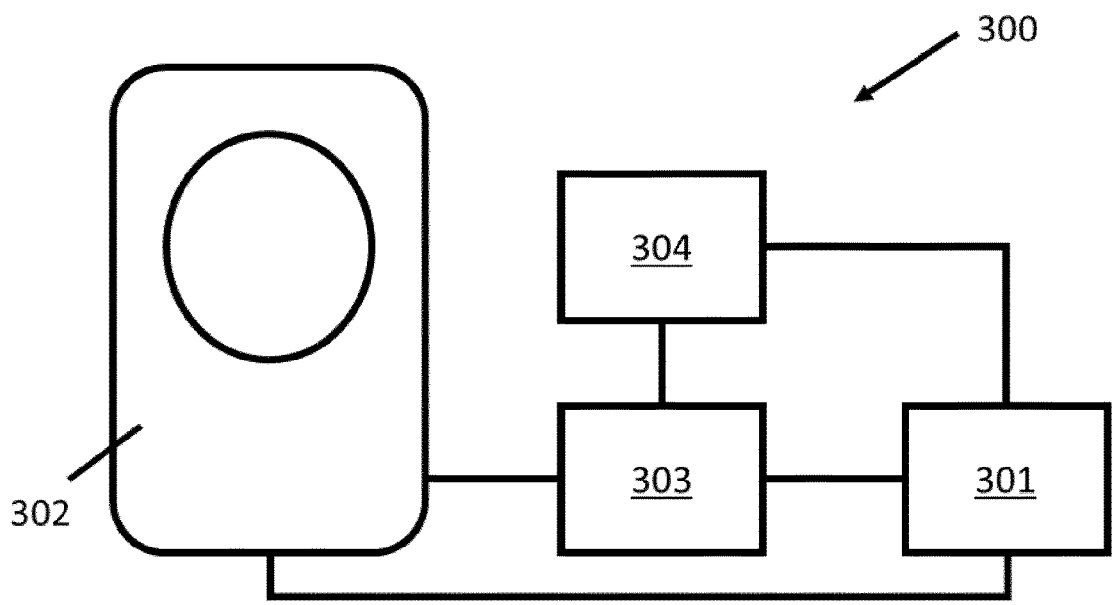
FIG. 3 shows a controller and a spectral scanning system comprising the same according to an embodiment of the present invention.

In another aspect, the present invention relates to a controller which is configured to perform the steps of selecting an image modality having a largest calculated contrast value, and/or calculating the contrast values for a given number of reconstructed image modalities and region of interest, and/or deriving a reconstruction modality from an imaging protocol based on a pre-detected lesion type and a current time stamp. Such a controller 301 is shown in FIG. 3. The controller 301 may be of a larger spectral scanning system 300 which also comprises a spectral CT scanner 302, a reconstruction unit 303, and a display 304.

The spectral CT scanner 302 may comprise a dual-layer energy-discriminating radiation detector or detector array. Alternatively a spectral scan gathering spectral, e.g. energy-resolved, projection data may be achieved through voltage switching of an X-ray source, through the interleaved or sequential use of two or more X-ray sources operating at different voltages, or through photon-counting detectors. The reconstruction unit 303 may comprise dedicated image processing means to run the computationally intensive reconstruction algorithms, e.g. acceleration hardware, GPUs or GPU arrays, special purpose signal processors, etc.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A method for spectrally imaging an organ during an image-guided intervention, comprising:
displaying a first image modality of a contrast-enhanced organ based on at least one first spectral scan of the contrast-enhanced organ;
receiving a selection of a region of interest within the displayed first image modality;
obtaining at least one second spectral scan of the contrast-enhanced organ;
obtaining at least three second image modalities;
determining a contrast value over the region of interest for each of the at least three second image modalities, the at least three second image modalities being based on the at least one second spectral scan;
selecting from the at least three second image modalities the second image modality with the largest contrast value; and
displaying the selected second image modality to provide a dynamic adaptation of the displayed second image modality such that a time interval available for guiding the image-guided intervention, before washout of a contrast agent, is prolonged.

2. The method according to claim 1, wherein determining the contrast value over the region of interest comprises determining a contrast ratio between a lesion of the contrast-enhanced organ and a surrounding parenchyma.

3. The method according to claim 2, further comprising deriving a signal representative of a hypervascularity or hypovascularity of the lesion based on the determined contrast ratio.

4. The method according to claim 1, further comprising boosting the contrast of the displayed image modality if the largest contrast value is determined lower than a pre-set reference value.

5. The method according to claim 1, further comprising:
performing at least one first spectral scan of a contrast-enhanced organ using the contrast agent and reconstructing the first image modality of the contrast-enhanced organ based on the at least one first spectral scan;
wherein obtaining the at least three second image modalities of the contrast-enhanced organ comprises performing at least one second spectral scan of the contrast-enhanced organ and reconstructing, from the at least one second spectral scan, the at least three second image modalities of the contrast-enhanced organ.

6. The method according to claim 5, wherein performing at least one first spectral scan further comprises triggering said at least one first scan, or wherein the at least one second spectral scan is triggered after performing the at least one first spectral scan with a predetermined time delay.

7. The method according to claim 1, further comprising obtaining the at least three second image modalities of the contrast-enhanced organ based on a plurality of further spectral scans for repeatedly adapting the displayed image modality by selecting, for each further spectral scan, the one of the at least three second image modalities with the largest contrast value over the region of interest for display.

8. The method according to claim 1, wherein the contrast-enhanced organ is a liver, and wherein obtaining a first imaging modality comprises obtaining a first imaging modality based on at least two first spectral scans, one in the artery phase and another one in the portal venous phase of the contrast-enhanced liver.

9. The method according to claim 1, wherein at least one of the second image modalities is one of virtual non-contrast, effective atomic number, iodine, monoenergetic at a predetermined energy level.

10. The method according to claim 1, wherein a time stamp is obtained for the at least one second spectral scan and wherein the contrast value is being determined using the time stamp and an imaging protocol corresponding to a predetermined lesion type predicting which of the at least three second image modalities has the largest contrast value.

11. The method according to claim 10, wherein a predetermined set of lesion types comprises at least one of metastasis, hepatocellular carcinoma of type I, hepatocellular carcinoma of type II, Hemangioma, cyst.

12. The method according to claim 10, wherein at least one of the at least three second image modalities is at least one of virtual non-contrast, effective atomic number, iodine, monoenergetic at a predetermined energy level, or wherein a reference time for timestamping spectral scans is determined as a moment in time at which the contrast agent is injected.

13. A controller configured to carry out the method of claim 1.

14. A spectral scanning system configured to carry out the method of claim 1, and further comprising a spectral computed tomography (CT) scanner and a display device for displaying selected image modalities.

* * * * *